United States Patent [19]

Calne

[11] Patent Number: 5,100,899
[45] Date of Patent: Mar. 31, 1992

[54] METHODS OF INHIBITING TRANSPLANT REJECTION IN MAMMALS USING RAPAMYCIN AND DERIVATIVES AND PRODRUGS THEREOF

[76] Inventor: Sir R. Calne, 22 Arrow Road, Cambridge, England, CB22AS

[21] Appl. No.: 362,354

[22] Filed: Jun. 6, 1989

[51] Int. Cl.$^5$ .............................................. A61K 31/44
[52] U.S. Cl. ..................................................... 514/291
[58] Field of Search ......................... 424/122; 514/291

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,688 | 2/1982 | Rakhit | 424/122 |
| 4,650,803 | 3/1987 | Stella et al. | 514/291 |

OTHER PUBLICATIONS

Chemical Abstracts 112:353y (1990).
Martel, R. R., et al., Can. J. Physio. Pharmacol. 55:48–51 (1977).
Staruch, M. J., et al., FASEB. J. 3(3):3411 (1989).
Dumont, *FASEB Journal*, vol. 3, #5256.

*Primary Examiner*—Jerome D. Goldberg
*Attorney, Agent, or Firm*—Darby & Darby

[57] ABSTRACT

This invention provides a method of inhibiting organ or tissue transplant rejection in a mammal in need thereof, comprising administering to said mammal a transplant rejection inhibiting amount of rapamycin. Also disclosed is a method of inhibiting organ or tissue transplant rejection in a mammal in need thereof, comprising administering to said mammal (a) an amount of rapamycin in combination with (b) an amount of one or more other chemotherapeutic agents for inhibiting transplant rejection, e.g., azathioprine, corticosteroids, cyclosporin and FK506, said amounts of (a) and (b) together being effective to inhibit transplant rejection and to maintain inhibition of transplant rejection.

7 Claims, No Drawings

METHODS OF INHIBITING TRANSPLANT REJECTION IN MAMMALS USING RAPAMYCIN AND DERIVATIVES AND PRODRUGS THEREOF

FIELD OF THE INVENTION

This invention relates to methods of inhibiting organ or tissue transplant rejection in mammals. More particularly, the invention relates to methods of inhibiting transplant rejection in mammals in need thereof, comprising administering to such mammals a transplant rejection inhibiting amount of rapamycin.

BACKGROUND OF THE INVENTION

Rejection and infective complications resulting from immunosuppressive treatment are the principal causes of failure of organ allografting in man, that is, an organ graft made between two genetically different individuals in the same *Homo sapiens* species. In order to minimize the individual specific side-effects of the three effective agents used in clinical practice, namely azathioprine, corticosteroids and cyclosporin, small doses of each are used in combination "triple therapy". Of the three agents currently used in such triple therapy, cyclosporin is the most powerful, but has the unsatisfactory side-effect of nephrotoxicity in man which can lead to structural renal damage. Increased corticosteroid dosage and antilymphocyte antibody preparations, poly- or monoclonal, are used for the treatment of rejection crises. A number of studies have been taken to investigate other potentially effective compounds for use as immunosuppressants and transplant rejection inhibitors, but to date, none have been found to be useful in clinical settings because of side-effects, such as toxicity, the lack of efficacy or a combination of these factors.

The fungal product FK506 was reported to have immunosuppressive activity in animals with organ grafts (Ochiai, T., et al., *Transplant. Proc.*, Vol. XX, No. 1, pp. 209-214, 1988). Although the immunosuppressive activity of FK506 was confirmed, the toxicity in mammals, such as rats, pigs and dogs, and in primates, e.g., baboons, was too severe to proceed to clinical phase trials (Collier, D. St. J., et al., *Transplant. Proc.*, Vol. XX, No. 1, pp. 226-228, 1988).

It would be extremely useful to discover a compound having immunosuppressive activity which could be employed to increase transplant acceptance in a recipient but without causing serious toxic side effects typically associated with conventional immunosuppressant therapy, such as those discussed above.

Rapamycin is a lipophilic macrolide with certain structural similarities to FK506 produced by *Streptomyces hygroscopicus* with both antifungal and antitumor properties (Sehgal, S. N. et al., *J. Antibiot.*, Vol. 28, pp. 727-732, 1975; Eng. C. P., et al., *J. Antibiot.*, Vol. 37, pp. 1231-1237, 1984).

It was reported that rapamycin inhibited two experimental immunopathies, i.e., experimental allergic encephalitis and adjuvant arthritis, and the formation of humoral (IgE-like) antibody. (Martel, R. R., et al., *Can. J. Physio. Pharmacol.*, 55: 48-51, 1977) It has also been reported recently that rapamycin inhibits murine T cell activation, apparently through a different mechanism from FK506 (Staruch, M. J., et al., *The FASEB Journal*, Vol 3, No. 3, abstract #3411, 1989). In addition, it was disclosed that rapamycin blocks the immunosuppressive effect of FK506 but not that of cyclosporin A (Dumont, F. J. et al., *The FASEB Journal*, Vol. 3, No. 4, abstract #5256, 1989). There was no teaching or suggestion in these reports, however, that rapamycin could or should be used to effectively inhibit organ or tissue transplant rejection in mammals. Furthermore, these reports do not disclose or intimate that the toxic side-effects associated with FK506, and other immunosuppressive agents, would not likewise arise from administering rapamycin as an agent to inhibit transplant rejection in transplant operations.

OBJECTS OF THE INVENTION

It is an object of this invention to provide a method of increasing allograft acceptance (or inhibiting organ or tissue transplant rejection) in mammals by administering an efficacious compound of low toxicity.

It is another object of this invention to reduce the toxicity of other conventional chemotherapeutic agents for inhibiting transplant rejection by combining their administration with an efficacious compound of low toxicity.

These and other objects of the invention will become clearer in light of the detailed description which follows.

SUMMARY OF THE INVENTION

The present inventor has discovered a method of inhibiting organ or tissue transplant rejection in a mammal in need thereof, comprising administering to said mammal a transplant rejection inhibiting amount of rapamycin.

The present inventor has also discovered a method of inhibiting organ or tissue transplant rejection in a mammal in need thereof, comprising administering to said mammal (a) an amount of rapamycin in combination with (b) an amount of one or more other chemotherapeutic agents for inhibiting transplant rejection, said amounts of (a) and (b) being effective to inhibit transplant rejection and to maintain inhibition of transplant rejection.

DETAILED DESCRIPTION OF THE INVENTION

All patents and literature references are hereby incorporated by reference in their entirety.

The present invention provides a method of inhibiting organ or tissue transplant rejection in a mammal in need thereof, comprising administering to said mammal a transplant rejection inhibiting amount of rapamycin.

The present invention also provides a method of inhibiting organ or tissue transplant rejection in a mammal in need thereof, comprising administering to said mammal an amount of rapamycin effective to inhibit transplant rejection and to maintain inhibition of transplant rejection.

As used herein, the terms "inhibiting organ or tissue transplant rejection" and "maintain inhibition of transplant rejection" refer to increasing organ or tissue transplant acceptance (or decreasing the likelihood of organ or tissue transplant rejection) involving allografts, i.e., transplantation of organs or tissues from donor to recipient both of whom are in the same species (intraspecific), such as *Homo sapiens*.

Rapamycin is an antifungal antibiotic which is extractable from a streptomycete, e.g., *Streptomyces hygroscopicus*. Methods for the preparation of rapamycin are disclosed in Sehgal et al., U.S. Pat. Nos. 3,929,992, and 3,993,749. In addition, monoacyl and diacyl derivatives of rapamycin and methods for their preparation are disclosed by Rakhit, U.S. Pat. No. 4,316,885. Furthermore, Stella et al., U.S. Pat. No. 4,650,803 disclose water soluble prodrugs of rapamycin, i.e., rapamycin derivatives including the following rapamycin prodrugs: glycinate prodrugs, propionate prodrugs and the pyrrolidino butyrate prodrugs.

The methods and compositions of the present invention include the use of natural and synthetic rapamycin, genetically engineered rapamycin and all derivatives and prodrugs of rapamycin, such as described in the aforementioned U.S. patents, U.S. Pat. Nos. 3,929,992; 3,993,749; 4,316,885; and 4,650,803, the contents of which are hereby incorporated by reference.

The present inventor has noted the efficacy of rapamycin in inhibiting transplant rejection, e.g., by depressing the immune system in mammals without the attendant toxic side-effects associated with other conventional immunosuppressive agents, e.g., azathioprine, corticosteroids and cyclosporin. Among such toxic side-effects are nephrotoxicity, severe leukopenia, thrombocytopenia, Cushing's Syndrome and diabetes.

It has been discovered that rapamycin reduces or inhibits allograft rejection in mammals, i.e., organ or tissue transplantation from donor to recipient of the same species. Among such transplanted organs or tissues and given illustratively, are heart, liver, kidney, spleen, lung, small bowel, pancreas, and bone marrow, or a combination of any of the foregoing.

As used herein, the term "transplant rejection inhibiting amount" refers to the amount of rapamycin (or of rapamycin in combination with one or more other chemotherapeutic agents for inhibiting transplant rejection) which may be administered so as to inhibit transplant rejection in a mammal and to maintain transplant rejection inhibition, without causing severe toxic side-effects, e.g., nephrotoxicity, renal failure, etc. Those skilled in the art will appreciate that the dosage or amount of a transplant rejection inhibiting compound which is administered to a subject about to undergo or having undergone an organ or tissue transplant, will vary according to a number of factors, including individual characteristics, such as weight, age, and other factors, such as the type of organ or tissue transplanted or about to be transplanted.

In one aspect of this invention, a tissue rejection inhibiting amount of rapamycin comprises from about 0.5 to about 50 mg/kg/day, preferably from about 1 to about 5 mg/kg/day. In another aspect, the inhibiting transplant rejection amount of rapamycin is administered for a period of time comprising from about 1 to about 180 days, or longer, as necessary. Those skilled in the art will recognize that compounds, drugs, agents, and the like, for inhibiting transplant rejection, may be administered to a subject mammal, e.g., a human, for an indefinite post-transplantation period, in some instances, for the lifetime of the subject, provided, of course, that the subject is tolerating the compound, drug, agent, etc., reasonably well without serious side-effects.

Rapamycin may be administered either orally or parenterally, e.g., intramuscularly, intraperitoneally, subcutaneously, or intravenously to a mammal subject. The preferred route of administration is oral.

According to this invention, rapamycin may be administered in various pharmaceutical forms, including pharmaceutical forms suitable for injectable use, such as sterile aqueous solutions or dispersions and sterile powders for the preparation of sterile injectible solutions or dispersions. In addition, rapamycin may be administered in tablets, caplets, capsules, and the like for convenient oral administration. Rapamycin may be administered in a pharmaceutically compatible or acceptable carrier, which includes by way of non-limiting example, oils, e.g., olive oil, alcohol, propylene glycol, and surfactants, such as Chemophor EL (BASS).

Another useful feature of this invention resides in the administration of rapamycin in combination with other conventional drug therapies, such as "triple therapy," azathioprine (available from Burroughs Wellcome Co., Research Triangle Park, N.C., under the tradename Imuran®), corticosteriods (available from the Upjohn Company, Kalamazoo, Michigan, under the tradename Solu-Medrol®); cyclosporin (and cyclosporin A) (available from Sandoz Pharmaceuticals, East Hanover, New Jersey, under the tradename Sandimmune®), and also FK506, (available from Fujisawa Pharmaceutical Co., Ltd., Osaka, Japan, under the tradename Fujimycin®). By combining rapamycin with such other conventional chemotherapeutic drugs or agents for inhibiting transplant rejection, the toxicity of the latter may be advantageously reduced in that lesser amounts of such toxic drug or agents are required in order to inhibit transplant rejection in a mammalian transplant subject either before or after transplantation, and also to maintain inhibition of transplant rejection.

Thus, the present invention provides a method of inhibiting transplant rejection in a mammal in need thereof, comprising administering to said mammal (a) an amount of rapamycin in combination with (b) an amount of one or more other chemotherapeutic agents for inhibiting transplant rejection, the amounts of (a) and (b) together being effective to inhibit transplant rejection and to maintain inhibition of transplant rejection. It should be understood that the amount of either (a) or (b) alone, might or might not be effective in inhibiting and maintaining transplant rejection. The combination of the two components (a) and (b), together, however, is effective to inhibit transplant rejection and to maintain inhibition of transplant rejection.

Therefore, is used herein, such "other" chemotherapeutic agents for inhibiting transplant rejection include, for example, azathioprine, corticosteroids, cyclosporin (and cyclosporin A), and FK506, or a combination of any of the foregoing.

The various features of the invention described above, such as the type of organ or tissue which is transplanted; the amount effective to inhibit transplant rejection and to maintain inhibition of transplant rejection; the mode or route of administration; and the duration of treatment; apply to the method of inhibiting organ or tissue transplant rejection by administering rapamycin in combination with one or more other chemotherapeutic agents for inhibiting transplant rejection and to maintain inhibition of transplant rejection.

In addition, however, it should be understood that such other chemotherapeutic agents may be administered continuously or intermittently with rapamycin. Furthermore, the route of administration may differ from that employed for rapamycin. That is to say, such other chemotherapeutic agents may be administered parenterally while rapamycin is being administered orally to the mammalian subject.

The present invention is described below in specific working examples which are intended to illustrate the invention without limiting its scope.

EXAMPLE 1

Organ Allograft Studies

Rats: Heterotopic heart allografts were performed from DA donor to PVG recipients. DA and PVG refer to specific rat strains. Rapamycin was administered intramuscularly in olive oil for the first 10 postoperative days except for Group 6 which only received the drug on days 3-6 postoperatively. Graft survival was assessed by daily palpation.

Large Animals: On the basis of the initial toxicity study two experiments were considered suitable to test whether rapamycin was immunosuppressive, namely, a short term dosing in dogs following renal transplantation and indefinite dosing of pigs, again following renal grafting.

Pigs: In pigs an orthotopic renal transplantation model was used and Mixed Lymphocyte Cultures (MLC) were performed to confirm histoincompatibility between donor and recipient. Untreated controls mean survival time is less than 10 days. Rapamycin was administered at a dose of 2mg/kg orally daily commencing on the first postoperative day.

Results:

Allograft Studies
Rat:

oil at a maximum concentration of 15 mg/ml and administered by daily intramuscular injection at dose schedules varying from 0.5 mg/kg to 50 mg/kg for ten consecutive days and in the last group at 10 mg/kg on days 3 to 6. Graft survival was assessed by daily palpation of the heart.

Rapamycin prolonged allograft survival at all doses tested. Although there was some loss of weight this was not as marked as that found when FK506 was administered to rats.

Dogs

In dogs dosing at all levels induced a vasculitis and at doses greater than 0.25 mg/kg this led to such severe manifestations that they were killed before the end of the 28 day study. At the higher doses the vasculitis affected the gastrointestinal tract, interestingly, it also caused a thrombocytopaenia. Marked depletion of cells in the lymphoid tissue, particularly B cells, occurred. In the dog, toxicity due to a vasculitis, that appears to have a particular predilection for the gastrointestinal tract, made it impossible to assess the immunosuppressive effects of the drug in this particular model. This species-specific reaction to rapamycin confirmed similar unpublished observations of the inventor and his associates.

Pigs

Survival and cause of death are shown in Table 2 with current creatinine values.

TABLE 2

SURVIVAL OF PIG ALLOGRAFTS RECEIVING RAPAMYCIN 2 mg/Kg/DAY ORALLY IN DAYS AND CURRENT CREATININE

| | SURVIVAL | RENAL HISTOLOGY | CREATININE | OUTCOME | CAUSE OF DEATH | DAY LAST DOSED |
|---|---|---|---|---|---|---|
| 1 | >51 | | 217 | ALIVE | | 43 |
| 2 | >66 | | 193 | ALIVE | | 52 |
| 3 | >72 | | 283 | ALIVE | | 64 |
| 4 | 4 | ACUTE REJECTION | 1,410 | DIED | REJECTION | 4 |
| 5 | 5 | INFARCTION | | DIED | INFARCTION | 5 |
| 6 | 48 | FOCI PYELONEPHRITIS | 161 | DIED | INTERSTITIAL PNEUMONITIS | 47 |
| 7 | 49 | MILD ATN | 235 | DIED | INTERSTITIAL PNEUMONITIS | 48 |
| 8 | 50 | MILD ATN | 176 | DIED | INTERSTITIAL PNEUMONITIS | 49 |
| 9 | 55 | EARLY MILD REJECTION | 239 | DIED | INTERSTITIAL PNEUMONITIS | 51 |
| 10 | 63 | MODERATE ATN | 283 | DIED | INTERSTITIAL PNEUMONITIS | 62 |

For the rat, survival of allografts is shown in Table 1.

TABLE 1

SURVIVAL OF HETEROTOPIC CARDIAC ALLOGRAFTS IN RATS

| Group 1 | No. Rats | Dose Schedule | Survival (days) |
|---|---|---|---|
| 1 | 4 | 50 mg/kg × 10 d | 75*, 88*, 100(× 2) |
| 2 | 4 | 10 mg/kg × 10 d | 65, 77, 88, 100 |
| 3 | 4 | 2 mg/kg × 10 d | 58, 59, 59, 66 |
| 4 | 4 | 1 mg/kg × 10 d | 34, 49, 52, 55 |
| 5 | 4 | 0.5 mg/kg × 10 d | 19, 20, 20, 35 |
| 6 | 5 | 10 mg/kg d3-6 | 15, 19, 19, 19, 21 |

N.B. Rapamycin was administered intramuscularly in olive oil.
(18 mg/ml and 10 mg/ml suspensions used.)

N.B. Rapamycin was administered intramuscularly in olive oil. (18mg/ml and 10mg/ml suspensions used.)

Rat strains used: DA donors in PVG recipients. control rejection time (n=10)=7.4 days.

Explanation of Table 1: Heterotopic heart allografts in the neck of the rats were performed from DA donors to PVG recipients using the surgical techniques previously described (Heron, I., *Acta, Pathol. Microbiol. Scand.* 79:366, 1971). Rapamycin was dissolved in olive Explanation of Table 2: Orthotopic kidney transplantation with contralateral nephrectomy was performed in the pig, as previously described (Calne, R. Y. et al., *Brit. J. Surg.*, 59: 969-977 (1972). Donor and recipient pairs were obtained from litters with different parents and incompatibility at the Major Histocampatibility Complex (MHC) was confirmed by the mixed lymphocyte reaction (Bradley, B. A., et al., *Tissue Antigens*, 4: 283-290, 1974). Rapamycin was administered orally at 2 mg/kg/day dissolved in olive oil at a concentration of 10 mg/ml.

In the case of pigs, one died of accelerated acute rejection and one died due to technical failure. The remaining eight animals recovered well and after an initial weight loss of approximately 10%. Subsequently, at about day 50 5 animals developed anorexia, diarrhea and became unwell to the extent that it was decided that they should be killed. Histological examination of these animals revealed that they were suffering from interstitial pneumonitis, probably due to over-immunosuppression, and this was the reason that they became unwell.

Furthermore, the renal histology did not show evidence of rejection except a mild degree in one animal who had not received the drug for 4 days. Histological examination of the colons in these animals showed mucosal and submucosal edema but no vasculitis and no ulceration. Thus this was probably secondary to the systemic effects of the pneumonitis. The remaining three animals continued to thrive, all dosing having being stopped as indicated in Table 3.

Discussion

Rapamycin was immunosuppressive and not toxic in the rat down to a dose of 0.5mg/kg although the compound was more effective at higher doses.

In pigs, the results of the toxicity study showed that the drug was tolerated at a dose of 1 mg/kg in that both animals gained weight. On histological examination colitis was seen but no vasculitis was found or suggested. Rapamycin was effective as an immunosuppressive agent but after about 50 days of continuous dosing at 2 mg/kg, 50% of the animals developed interstitial pneumonitis due to over-immunosuppression, and these animals were killed. However, none of the animals showed any evidence of ulceration in the colon or vasculitis. Therefore, in future studies monitoring of blood drug levels will be of benefit.

In conclusion, rapamycin is a very effective immunosuppressive agent which can be employed to inhibit allograft transplantation rejection in mammalian subjects.

What is claimed is:

1. A method of inhibiting organ or tissue transplant rejection in a mammal in need thereof, comprising administrating to said mammal a transplant rejection inhibiting amount of rapamycin.

2. The method according to claim 1, wherein a transplant rejection inhibiting amount of rapamycin is administered in an amount comprising from about 0.5 to about 50 mg/kg/day.

3. The method according to claim 2, wherein said amount comprises from about 1 to about 5 mg/kg/day.

4. The method according to claim 1, wherein said rapamycin is administered for a period of time comprising from about 1 to about 180 days.

5. The method according to claim 1, wherein said rapamycin is administered orally.

6. The method according to claim 1, wherein said rapamycin is administered parenterally.

7. The method according to claim 1, wherein said rapamycin is administered for an indefinite period of time to maintain inhibition of transparent rejection.

* * * * *

UNITED STATES PATENT AND TRADEMARK OFFICE
CERTIFICATE OF CORRECTION

PATENT NO. : 5,100,899
DATED : March 31, 1992
INVENTOR(S) : Sir R. Calne

It is certified that error appears in the above-indentified patent and that said Letters Patent is hereby corrected as shown below:

Column 8, line 25:
Claim 7, change, "transparent" to --transplant--.

Signed and Sealed this

Sixteenth Day of August, 1994

Attest:

BRUCE LEHMAN

*Attesting Officer*          *Commissioner of Patents and Trademarks*